US00PP24550P3

(12) United States Plant Patent
Leis et al.

(10) Patent No.: US PP24,550 P3
(45) Date of Patent: Jun. 17, 2014

(54) APPLE TREE NAMED 'GAIA'

(50) Latin Name: ***Malus domestica* Mill.**
Varietal Denomination: Gaia

(75) Inventors: Michelangelo Leis, Ferrara (IT); Alessio Martinelli, Ferrara (IT); Francesco Tagliani, Argenta (IT); Gianfranco Castagnoli, Quingentole (IT); Donata Azzolini, legal representative, Quingentole (IT); Pietro Castagnoli, legal representative, Quingentole (IT); Alessandro Castagnoli, legal representative, Quingentole (IT)

(73) Assignee: C.I.V.—Consorzio Italiano Vivaisti—Societá Consortile A R.L., Comacchio FE (IT)

( * ) Notice: Subject to any disclaimer, the term of this patent is extended or adjusted under 35 U.S.C. 154(b) by 78 days.

(21) Appl. No.: 13/385,524

(22) Filed: Feb. 24, 2012

(65) Prior Publication Data

US 2013/0031683 P1 Jan. 31, 2013

(30) Foreign Application Priority Data

Jul. 26, 2011 (QZ) ..... 20111879

(51) Int. Cl.
*A01H 5/00* (2006.01)

(52) U.S. Cl.
USPC ..... Plt./161

(58) Field of Classification Search
USPC ..... Plt./161
See application file for complete search history.

(56) References Cited

PUBLICATIONS

Jankovic, P. "Sweet Resistance," Fruit, Review for Fruit Growing, Viticulture, and Enology, vol. No. 12, Issue No. XXI, Dec. 2010, pp. 9-10 (translation provided).*

* cited by examiner

*Primary Examiner* — Susan McCormick Ewoldt
(74) *Attorney, Agent, or Firm* — Foley & Lardner LLP

(57) ABSTRACT

A new and distinct *Malus domestica* Mill. apple tree variety named 'Gaia' particularly characterized by moderately vigorous tree with good habit. Highly productive with precocious fruit bearing. Resistant to scab. The fruit is big, larger than Gala, with a regular, rounded, slightly flattened shape. Less subject to cracking then Gala. Yellowish-green ground colour with striped red overcolour. The flesh is creamy, fine, crispy and juicy. The flavour is good, very sweet, similar to Galaxy but with a more intense aroma. Storage life comparable to Galaxy.

4 Drawing Sheets

Latin name of the genus and species of the plant claimed: *Malus domestica* Mill.

Variety denomination: 'GAIA'.

PRIORITY CLAIM

This application claims priority to European Community Plant Variety Office Application No. 2011/1879, filed Jul. 26, 2011.

BACKGROUND OF THE INVENTION

The present invention relates to a new and distinct variety of apple tree, botanically known as *Malus domestica* Mill. of the Family Rosaceae, and hereinafter referred to by the variety denomination 'Gaia'.

The new *Malus* variety is a product of a planned breeding program conducted by the inventors, Michelangelo Leis, Alessio Martinelli, Gianfranco Castagnoli and Francesco Tagliani in S. Giuseppe di Comacchio (Ferrara), Italy. The objective of the breeding program was to develop new *Malus* varieties with improved production characteristics, high-quality flavour and aroma, and sustainability by increasing the tree's natural resistance. The primary objective of the research programme is to selection new apple varieties with natural resistances, in particular to scab.

The new *Malus* variety, 'Gaia', originated from a cross made in a planned, controlled breeding program in S. Giuseppe di Comacchio (Ferrara), Italy. The female parent is 'Gala' variety (unpatented). The male parent is an unpatented proprietary selection denominated 'A3-7'. 'Gaia' was discovered and selected in August 2004 by the inventors as a flowering plant within the progeny of the stated cross in a controlled environment in S. Giuseppe di Comacchio (Ferrara), Italy.

Asexual reproduction of the new *Malus* variety by budding and grafting was first performed in September 2004 and in the following years in S. Giuseppe di Comacchio (Ferrara), Italy, and has demonstrated that the combination of characteristics as herein disclosed for the new *Malus* variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'Gaia' which in combination distinguish this apple tree as a new and distinct variety:

1. Slightly flattened shape;
2. Intense striped red overcolour;
3. Scab resistance;

4. Medium vigor, open habit with short branches;
5. Good flavor, very sweet with intense aroma and
6. Good storage ability.

Of the commercial cultivars known to the inventors, the most similar in comparison to 'Gaia' is the variety 'Galaxy' (Patented, U.S. Plant Pat. No. 6,955). In comparison to the similar variety 'Galaxy', 'Gaia' differs primarily in the traits listed in Table 1:

TABLE 1

Comparison with Similar Variety

| Denomination of similar variety | Characteristic in which the similar variety is different | State of expression of similar variety | State of expression of candidate variety |
|---|---|---|---|
| Galaxy | General shape | conic | regular, rounded, slightly flattened. |
| | Relative area of over colour | Medium | Large |
| | Resistance to disease | No | Scab resistant |

When the current variety 'Gaia' is compared to the parent varieties 'Gala' and 'A3-7', the varieties differ in the characteristics presented in Table 2:

TABLE 2

Comparison with Parent Varieties

| Characteristic in which the variety is different | State of expression of candidate variety | The female parent ('Gala') | The male parent ('A3-7') |
|---|---|---|---|
| Resistance to Scab | Yes | No | Yes |
| Fruit over color | Red | Light Red | Medium Red |
| Relative area of over color | Large | Medium | Medium to large |
| Pattern of over color | Solid flush with weakly defined stripes | Solid flush with weakly defined stripes | Only solid flush |
| Fruit shape | Rounded, slightly flattened | Conic | Short-conic to round |
| Eating maturity | Medium | Medium | Medium to late |

The current variety 'Gaia' can also be meaningfully compared to the variety 'Gemini' (Patented, U.S. Plant Pat. No. 24,091) as they share the same parent varieties ('Gala' and 'A3-7'). The varieties 'Gaia' and 'Gemini' differ in the characteristics presented in Table 3:

TABLE 3

Comparison with Similar Variety 'Gemini'

| Characteristic in which the variety is different | State of expression of candidate variety | State of expression of 'Gemini' |
|---|---|---|
| Resistance to Scab | Yes | Yes |
| Fruit over color | Red (RHS 47A) | Red (RHS 46A) |
| Relative area of over color | Large | Very Large |
| Pattern of over color | Solid flush with weakly defined stripes | Only solid flush |
| Fruit shape | Rounded, slightly flattened | Conic |
| Eating maturity | Medium | One week after 'Gaia' |

BRIEF DESCRIPTION OF THE DRAWINGS

The accompanying photographs illustrate the overall appearance of the new apple tree 'Gaia' showing the colors as true as is reasonably possible with color reproductions of this type. Color in the photographs may differ slightly from the color value cited in the detailed botanical description, which accurately describe the color of 'Gaia'.

DETAILED BOTANICAL DESCRIPTION

Figure 1:
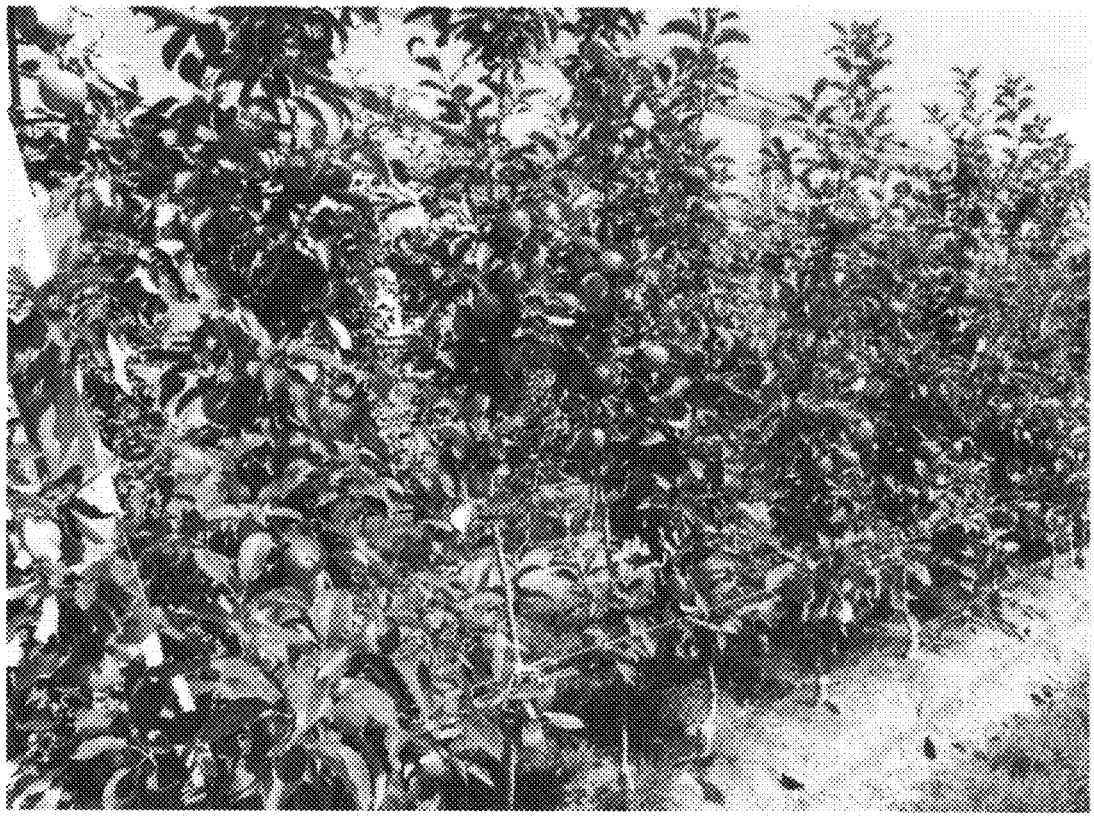
FIG. 1: illustrates the plant of 'Gaia'.
Figure 2:
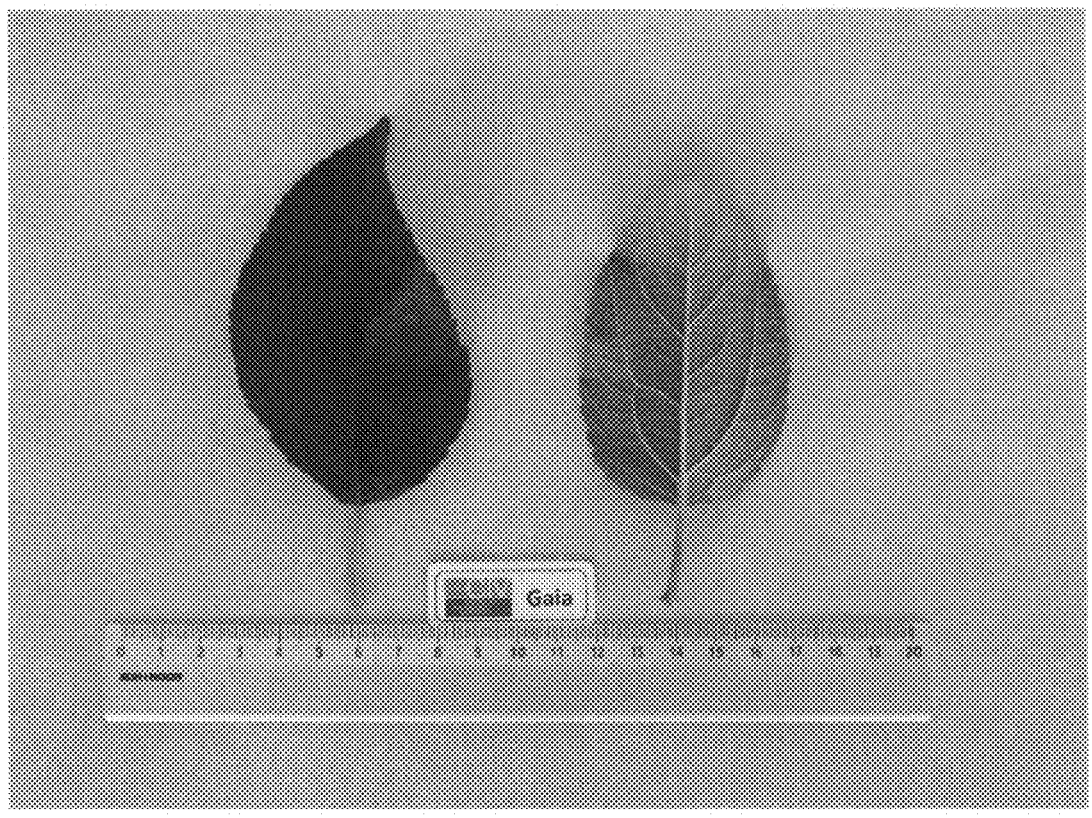
FIG. 2: illustrates the leaves of 'Gaia'.
Figure 3:
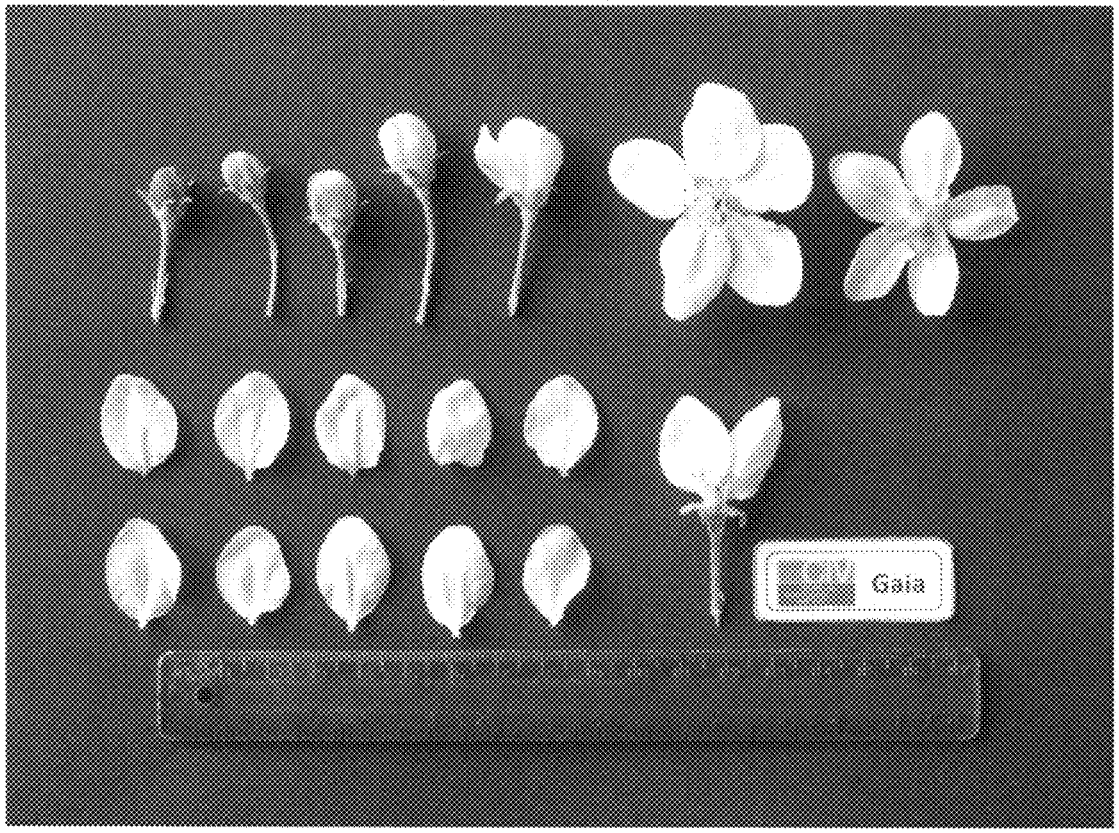
FIG. 3: illustrates the flowers of 'Gaia
Figure 4:
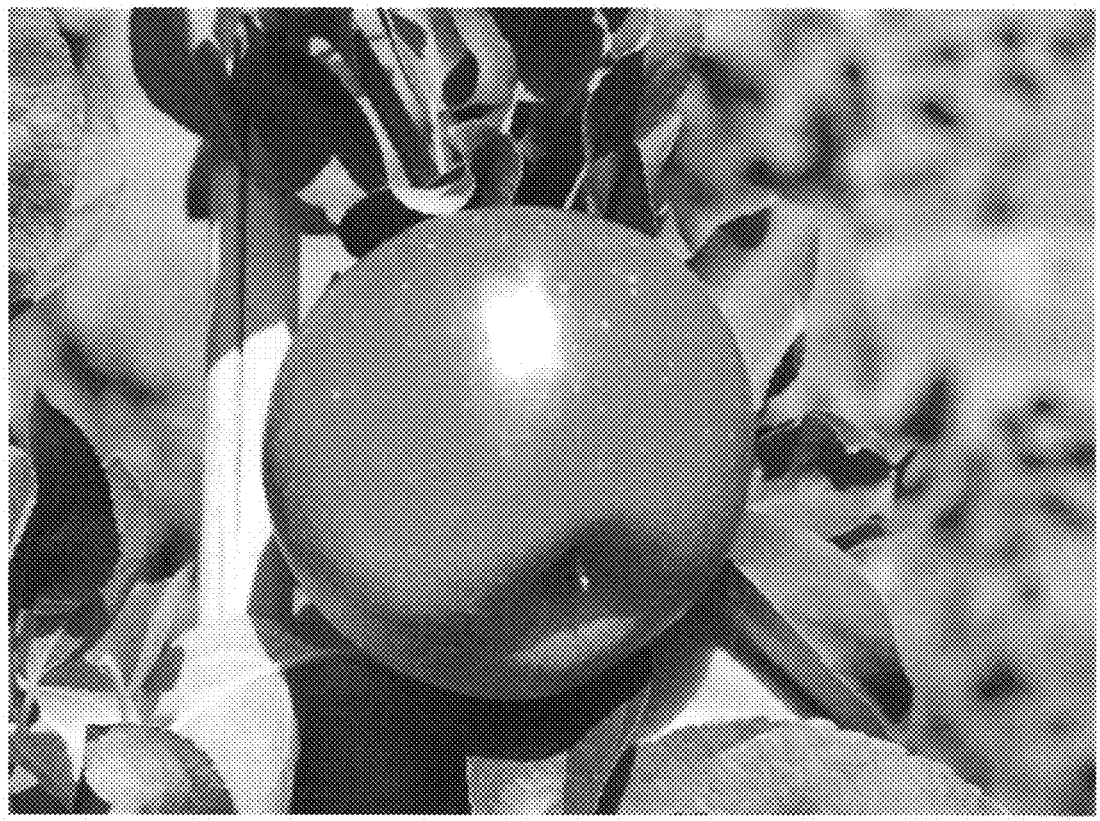
' and
FIG. 4: illustrates the fruits of 'Gaia'.

The new *Malus* variety 'Gaia' has not been observed under all possible environmental conditions. The phenotype of the new variety may vary with variations in environment such as temperature, light intensity, and day length without any change in the genotype of the plant.

The aforementioned photographs, together with the following observations, measurements and values describe the new *Malus* variety 'Gaia' as grown in the apple farm in S. Giuseppe di Comacchio (Ferrara), Italy, under conditions which closely approximate those generally used in commercial practice. The apple farm where 'Gaia' is grown is situated near the Adriatic sea (44°45' North, 12° 11' East) and is zero (0) meters above sea level. The soil of the apple farm where 'Gaia' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on four (4) year old 'Gaia' trees that were grown in the apple farm in S. Giuseppe di Comacchio (Ferrara), Italy, from 2007 to 2010 All trees were of cropping maturity. Quantified measurements are expressed as an average of measurements taken from a number of individual trees of 'Gaia'. The measurements of any individual tree, or any group of trees, of the new variety may vary from the stated average.

Color references are made to The Royal Horticultural Society Colour Chart (R.H.S.), first publication (1966), except where general colors of ordinary significance are used. Color values were taken under daylight conditions at approximately at 10:00 am in S. Giuseppe di Comacchio (Ferrara), Italy.

All trees of 'Gaia', insofar as they have been observed, have been identical in all the characteristics described below.

Classification:

*Botanical.*—*Malus domestica* Mill.

Parentage:

*Female parent.*—*Malus domestica* Mill. 'Gala' (unpatented).

*Male parent.*—*Malus domestica* Mill. 'A3-7' (unpatented proprietary selection).

Propagation: Budding and grafting on M9 rootstock.

Tree:

*Age*.—Observed plants were four years old.

*Vigor*.—Medium vigor.

*Tree type*.—Ramified.

*Habit*.—Spreading, branches angle is typically 45 to 75 degrees from the vertical stem.

*Density*.—Medium density.

*Cropping behavior*.—Precocious fruit bearing with high productivity.

*Type of bearing*.—Typically long shoot, presence of spur on 2-3 year old branches.

*Production*.—$4^{th}$ year: 16 Kg.

*Size*.—Height: 2.8 m. Spread: 1.30 m. Trunk Diameter: about 32 mm as measured 20 cm above point of grafting.

*Surface texture*.—Smooth.

*Bark color*.—Brown, RHS 197 C.

*Trunk lenticels*.—Overall Shape: elongated. Length: 1.8 mm. Width: 0.6 mm. Color: Yellow-brown RHS 164 C. Density: 2 to 3 per $cm^2$.

*Branches*.—Number per tree: about 22 at four (4) years. Length: Varies due to pyramidal shape of tree. At four (4) years, maximum of 90 cm to 110 cm; minimum of 30 cm to 50 cm. Diameter (at 3 years): About 12 mm to 15 mm. Surface texture: smooth. Color (at 3 years): greyed-green, RHS 197 C. Internode length: About 2.3 cm to 3.0 cm. Internode diameter: About 10 mm in the middle of branches.

*Branches lenticels*.—Overall Shape: rounded or slight elongated. Length: 0.7 mm. Width: 0.5 mm. Color: Yellow-brown, RHS 164 D. Density: About 5 per $cm^2$.

Leaves:

*Arrangement*.—Alternate, simple, petiolated.

*Lamina*.—Size: Length (4 year old): 90.7 mm (from $3^{rd}$ to $5^{th}$ fully expanded leaf). Width (4 year old): 56.7 mm (from $3^{rd}$ to $5^{th}$ fully expanded leaf).

*Length/width ratio*.—1.6. Overall Shape: elliptical. Base shape: rounded. Apex shape: acuminate. Margin: biserrate. Pubescence: absent on upper surface and weak pubescent on lower surface. Attitude in relation to shoot: outwards. Color (mature leaves): green, RHS 137 A on the upper side and 148 B underside.

*Venation*.—Type: prominent pinnate venation from a midrib to the edge. Color: green, RHS 148 C.

*Petiole*.—Length: about 25 mm. Diameter: 1.5 to 2.0 mm. Texture: hairy. Color: yellow-green, RHS 146 C with anthocyanin coloration.

*Stipule*.—Description: usually are not present; on some leafs are present but only in a side of the petiole. Small dimension.

Spur:

*Present*.—On 2-3 year old shoots.

*Distance between each spur*.—On the two-three year old branches, the distance is about 20 mm to 40 mm.

*Number of fruit per spur*.—2 to 4 without thinning.

Flowers:

*Blooming time*.—Full bloom on April $9^{th}$ in S. Giuseppe di Comacchio (Ferrara) in year 2011.

*Blooming period*.—8 to 12 days.

*Fragrance*.—Slight.

*Type*.—Inflorescence.

*Number of flowers per inflorescence*.—5 to 6.

*Flower size*.—Diameter: about 41 mm. Flower color: Primarily white, RHS 69 D, when petals fully opened, undersides of petals there are shades red-purple color, RHS 72 B, in the balloon stage red-purple, RHS 74 B.

*Buds*.—Number of buds per spur: typically, one on each spur. Shape: pointed. Length: about 8.0 mm. Width: about 5.0 mm. Color: brown, RHS 183 A with hairy surface.

*Petals*.—Arrangement: intermediate. Number per flower: typically five (5). Length: average 20.71 mm. Width: average 14.76 mm. Length/width ratio: 1.4. Overall shape: elliptic. Apex shape: obtuse. Base shape: rounded. Texture: smooth. Margin: entire. Color (upper surface): RHS 69 D. Color (lower surface): RHS 69 D with shade red-purple RHS 72 B.

*Sepals*.—Number per flower: five (5). Length: average 7.42 mm. Width: average 4 mm. Length/width ratio: 1.86. Overall shape: lanceolate. Apex shape: acute. Texture: hairy. Margin: entire. Color: green, RHS 138 B on upper surface and RHS 138 C lower surface.

*Pedicel*.—Length: average 27.6 mm. Diameter: about 1.5 mm. Texture: hairy. Color: green, RHS 138 B.

Fruit:

*Keeping quality*.—The fruit keeps well on the tree. The storage life is comparable to Gala.

*Maturity when described*.—Ripe for eating.

*Maturity period after full bloom*.—About 125 days in S. Giuseppe di Comacchio (Ferrara) Italy.

*Date of first and last pickings*.—About 12 August and 19 August in S. Giuseppe di Comacchio (Ferrara) Italy in year 2011.

*General shape*.—Regular, rounded, slightly flattened.

*Average weight*.—223.5 g.

*Fruit size*.—Average height: 65.9 mm. Average diameter (at widest point): 83 mm.

*Position of maximum diameter*.—In the middle of fruit.

*Height/diameter ratio*.—0.79.

*Stem*.—Length: average 26.1 mm. Diameter: average 2.2 mm. Color: yellow-green group, RHS 153 B.

*Stalk cavity*.—Depth: average 18.9 mm. Width: average 41.0 mm.

*Eye basin*.—Aperture of eye: fully open. Depth: average 10.3 mm. Width: average 34.1 mm. Crowning at calyx end: weak. Position of sepals: bent. Calyx tube: "V" form.

*Skin*.—Thickness: medium. Texture: smooth. Bloom: absent or very low. Greasiness: absent. Firmness (at picking time): 8 to 9 $kg/cm^2$. Overcolor color: red, RHS 47 A. Percentage of skin surface with overcolor color: large. Pattern of overcolor: solid flush with weakly defined stripes. Intensity of overcolor: medium. Ground color: yellow-green, RHS 154 C.

*Skin lenticels*.—Shape: round or slightly elongated. Length: about 0.6 mm. Width: about 0.6 mm. Color: yellow-white, RHS 158 B. Density: about 5 per $cm^2$ in the central area of the surface of fruit. The number of lenticels increases in a direction toward the hollow of the calyx and the size of the lenticels decreases.

*Flesh*.—Color: yellow, RHS 13 D. Texture: fine and juicy. Aroma: intense. Eating quality: the flavour is good, very sweet. Sugar content (at picking time): 13.5 to 14° Brix. Acidity/Starch (at picking time): Acidity: 4.5 to 5.5 g/lt Malic acid/starch: 2.5-3 Laimburg scale 1 to 5.

*Core*.—Symmetry of core: slightly asymmetric. Distinctness of core lines: evident. Locules: Number (per fruit): 5 (five). Length: 10.5 mm. Width: 4.5 mm. Form: moderately open.

Seeds:

*Number per fruit*.—6 to 10.

*Number per locule*.—About 1 to 3.

*Shape*.—Elliptic, elongated and pointed.

*Length*.—Average 8.0 mm.

*Width*.—Average 4.5 mm.

*Color*.—Brown, RHS 166 A.

Reproductive organs:

*Androecium*.—Stamens: Number per flower: about 20 (Twenty). Length: average 8.25 mm. Filament:

Length: about 7.0 mm. Color: green-white, RHS 157 B. Anther: Shape: ovoid, flat in the center. Length: 1.84 mm. Diameter: 1.43 mm. Color: yellow, RHS 8B. Pollen: Amount: abundant. Color: yellow, RHS 13 C. Requirements: the crab apple "*Malus* Evereste" is good pollinator.

*Gynoecium*.—Stigma: Shape: funnel shape with receptive surface on top. Length: 1.0 mm. Width: 0.4 mm. Color: Green, RHS 145 A. Style: Number per flower: 5 (Five). Length: about 9.0 mm. Width: about 0.3 mm. Color: yellow-green, RHS 138 B. Ovary: Length: about 3.0 mm. Width: about 3.0 mm. Color: green, RHS 138 B.

*Use*.—Fresh market.

*Sensitivity to disease/pests*.—Scab resistance.

*Winter hardiness*.—Tolerance to temperatures of −12° C. without observed damage to wood and buds of dormant apple trees; but open flowers and young fruitlets are killed by exposure to −3° C. to −5° C., depending on the length of exposure.

*Drought/heat tolerance*.—Good tolerance to heat, up to 40° C., growth is limited by drought periods without irrigation.

*Shipping/storage characteristics*.—Good storability under ULO-conditions (1° C., 2% $0_2$, 2% $CO_2$) for up to six (6) months.

We claim:

1. A new and distinct *Malus domestica* Mill. apple tree variety named 'Gaia', substantially as illustrated and described herein.

* * * * *